(12) United States Patent
Shibahara et al.

(10) Patent No.: US 8,959,461 B2
(45) Date of Patent: Feb. 17, 2015

(54) PATTERN MEASUREMENT DEVICE AND PATTERN MEASUREMENT METHOD

(75) Inventors: Takuma Shibahara, Tokyo (JP); Michio Oikawa, Tokyo (JP); Yutaka Hojo, Tokyo (JP); Hitoshi Sugahara, Tokyo (JP); Hiroyuki Shindo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/233,003

(22) PCT Filed: Mar. 23, 2012

(86) PCT No.: PCT/JP2012/057568
§ 371 (c)(1),
(2), (4) Date: Mar. 9, 2014

(87) PCT Pub. No.: WO2013/035364
PCT Pub. Date: Mar. 14, 2013

(65) Prior Publication Data
US 2014/0224986 A1 Aug. 14, 2014

(30) Foreign Application Priority Data
Sep. 8, 2011 (JP) .................................. 2011-195897

(51) Int. Cl.
*G06F 17/50* (2006.01)
*H01J 37/26* (2006.01)
*G01B 15/04* (2006.01)
*G03F 1/36* (2012.01)
*H01L 21/66* (2006.01)
*G01N 23/225* (2006.01)

(52) U.S. Cl.
CPC ............. *H01J 37/261* (2013.01); *G01B 15/04* (2013.01); *G03F 1/36* (2013.01); *H01L 22/12* (2013.01); *G01N 23/2251* (2013.01)
USPC .......................................................... 716/51

(58) Field of Classification Search
USPC .......................................................... 716/51
See application file for complete search history.

(56) References Cited

U.S. PATENT DOCUMENTS

2008/0127027 A1* 5/2008 Gallatin et al. ................ 716/19
2012/0328181 A1 12/2012 Kitamura et al.

FOREIGN PATENT DOCUMENTS

JP 2008-164593 A 7/2008

OTHER PUBLICATIONS

Lucas, K., "Optical Proximity Correction for Current and Future Nodes", SPIE Advanced Lithography Course Notes, SC990, Feb. 21-25, 2010, San Jose, California.

(Continued)

*Primary Examiner* — Suresh Memula
(74) *Attorney, Agent, or Firm* — Miles & Stockbridge P.C.

(57) ABSTRACT

A pattern measurement device includes: a storage section storing mask edge data of a circuit pattern and image data obtained by imaging the circuit pattern; an SEM contour extracting section receiving the image data, SEM contour of the circuit pattern, and cause an exposure simulator to generate estimated SEM contour data of an estimated SEM contour on the basis of the mask edge data and SEM contour data of the extracted SEM contour; a shape classifying section receiving the mask edge data, the SEM contour data, and the estimated contour data to classify the SEM contour data and the estimated SEM contour data into a one-dimensionally shaped contour and a two-dimensionally shaped contour; and an SEM contour sampling section receiving the SEM contour data and the estimated SEM contour data to sample the SEM contour data on the basis of types of the one-dimensionally and two-dimensionally shaped contours.

11 Claims, 15 Drawing Sheets

(56) References Cited

OTHER PUBLICATIONS

Shen, S., et al., "OPC Model Calibration Based on Circle-Sampling Theorem", IEEE Solid-State and Integrated Circuit Technology (2006).

Filitchkin, P., et al., "Contour Quality Assessment for OPC Model Calibration", Proceedings of SPIE, vol. 7272, pp. 72722Q1-72722Q7 (2009).

Shibahara, T., et al., "A CD-Gap-Free Contour Extraction Technique for OPC Model Calibration", Proceedings of SPIE, vol. 7971 (2011).

* cited by examiner

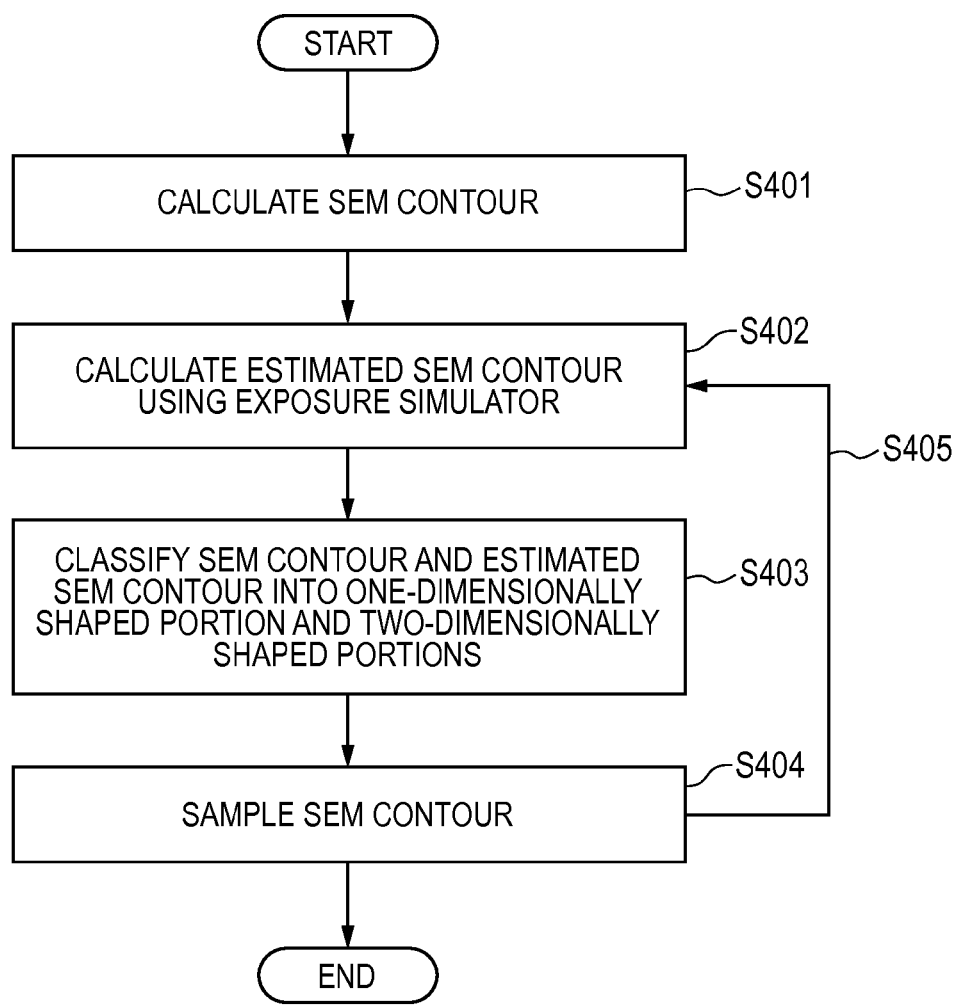

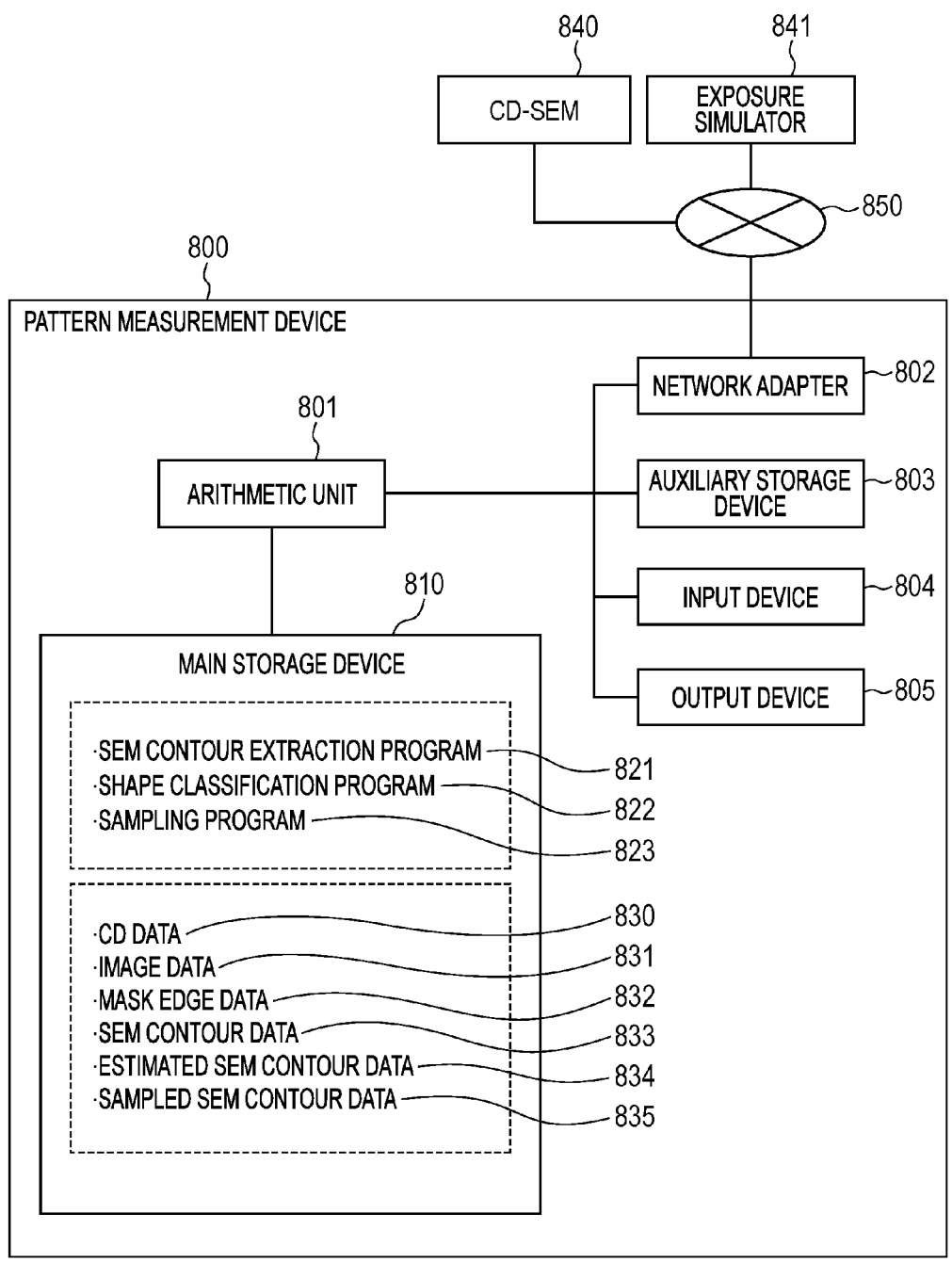

PATTERN MEASUREMENT DEVICE AND PATTERN MEASUREMENT METHOD

BACKGROUND

The present invention relates to a measurement device and a measurement method, and more particularly to a technique of analyzing an electron microscope image.

Semiconductor devices have been rapidly miniaturized and have reached the nanometer order in the early 2000s. Semiconductor devices are manufactured while various measurement devices typified by a critical dimension scanning electron microscope (CD-SEM) are used to measure the shape and dimensions of a circuit pattern in order to improve the yield of the products, and conform a difference between the circuit pattern and mask edge data. Especially, in a process (photolithography process) of transferring a photomask for the circuit pattern onto a wafer, it is important to measure the shape of the fine circuit pattern with high accuracy.

In the photolithography process, it is necessary to consider an optical proximity effect (optical diffraction effect) in order to form the circuit pattern of the nanometer order in accordance with the mask edge data of the circuit pattern. Regarding a simple mask shape 101 illustrated on the left side of FIG. 1A, a large difference between a shape 102 of a circuit pattern transferred on a wafer and a shape 103 of an edge of the mask shape 101 occurs due to the optical proximity effect, for example, as illustrated on the right side of FIG. 1A. In addition, a shape 104 of a corner is a round shape with recession tending to occur at an end of a line (EOL). A process (OPC: optical proximity correction) is introduced to change the photomask shape to a pattern shape 105 illustrated on the left side of FIG. 1B in order to obtain a desired pattern shape 106 illustrated on the right side of FIG. 1B. The OPC is a technique of improving the resolution of photolithography for correcting the shape of a transferred pattern by adjusting the width of a wiring and providing correction patterns for the EOL and the corner, for example.

Estimation of a parameter for a transfer model is required to apply the OPC to a photomask. According to a known document 1 (K. Lucas, "Optical Proximity Correction for Current and Future Nodes," SPIE advanced lithography short course, SC990, 2010.) and a known document 2 (S. Shen, et al., "OPC model calibration based on circle-sampling theorem," IEEE Solid-State and Integrated Circuit Technology, 2006.), a difference between an optical model and an actually exposed pattern occurs due to an effect of a resist, for example. Thus, the parameter for the transfer model is adjusted on the basis of a result of measurement of the length of a transfer pattern obtained by a CD-SEM. According to the known document 2, the series of processes are called OPC model calibration.

It is currently expected to achieve a method (hereinafter referred to as contour-based calibration) as one of new OPC model calibration methods. The method uses a CD value of a CD-SEM for a straight line portion of a circuit pattern to achieve two-dimensional positional coordinates of an SEM contour as calibration data for the other part of the circuit pattern. According to a known document 3 (P. Filitchkin, et al., "Contour quality assessment for OPC model calibration," Proceedings of SPIE, Vol. 7272, pp. 72722Q1-7, 2009.) and a known document 4 (T. Shibahara, et al., "CD-gap-free Contour Extraction Technique for OPC Model Calibration," Proceedings of SPIE, Vol. 7971, 2011.), in order to perform the contour-based calibration, it is necessary to measure an SEM contour that causes a short difference (hereinafter referred to as a CD-gap) between a conventional value and a CD measured length.

It is necessary to reduce the calibration time by sampling two-dimensional positional coordinate values of an SEM contour at appropriate intervals and reducing the amount of data since the calibration data in the OPC model calibration requires great time to analyze. The OPC model calibration with the data amount reduced, however, still has a problem with requiring several days to complete the process by a high-performance calculator.

If all SEM contour data is used for the OPC model calibration, the data amount to be calculated may be too large to be stored in a main storage device and to be processed depending on the performance of a calculator. It is necessary to reduce the SEM contour data amount for any of the problems to perform the contour-based calibration.

CITATION LIST

Patent Literature

PTL 1: Japanese Patent Application Laid-Open No. 2008-164593

SUMMARY

A first problem is described firstly. PTL 1 does not indicate a process of reducing the number of positions at which edges are calculated in a part (paragraph 0283) describing curve approximation/connection and the like that are performed after multiple points are detected at a second edge. Thus, the problem is to sample an SEM contour in order to at least reduce calculation time in the contour-based calibration.

Subsequently, a second problem is described. As described in PTL 1 and illustrated in FIG. 2A, in order to calculate positional coordinates of an SEM contour, a general process is that: the position of the center of a white band 202 is extracted as an image contour from an image 201; an image signal is extracted in a normal direction 204 of the image contour; and the SEM contour is measured after the extraction of the image signal. The image contour, however, tends to be distorted at a design stage such as an adjustment process of OPC and at the initial stage of a mass production stage. Due to the distorted image contour, a direction in which the length is measured may not be necessarily stable and may not be the normal direction 204 of the image contour. For example, the image signal may be extracted in normal directions 205 of the distorted image contour.

According to the known document 3, there is a report that the transfer accuracy of a one-dimensional characteristic (such as the width of a line and intervals between lines) of a mask pattern worsens when a two-dimensional SEM contour is used for the OPC model calibration. In order to solve this problem, according to the known document 4, it is important to reduce a difference (hereinafter referred to as CD-gap) between a CD value (hereinafter referred to as CDCD-SEM) obtained by a CD-SEM and a CD value (hereinafter referred to as CDContour) calculated from the SEM contour.

The SEM contour needs to be sampled without an increase in the CD-gap in order to solve the first problem and improve the accuracy of the OPC model calibration.

To solve the above two problems a pattern measurement device according to the present invention includes: a storage section configured to store mask edge data of a circuit pattern of a semiconductor and image data obtained by imaging the circuit pattern; an SEM contour extracting section configured to receive the image data, extract a scanning electron microscope (SEM) contour of the circuit pattern, and cause an exposure simulator to generate data (estimated SEM contour data) of an estimated SEM contour on the basis of the mask edge data and data (SEM contour data) of the extracted SEM contour; a shape classifying section configured to receive the mask edge data, the SEM contour data, and the estimated SEM contour data to classify the SEM contour data and the estimated SEM contour data into a one-dimensionally shaped contour and a two-dimensionally shaped contour; and an SEM contour sampling section configured to receive the SEM contour data and the estimated SEM contour data to sample the SEM contour data on the basis of types of the one-dimensionally and two-dimensionally shaped contours.

The present invention also provides a pattern measurement method performed by the pattern measurement device.

The present invention makes it possible to reduce calculation time required for OPC model calibration and improve the accuracy of the OPC model calibration.

BRIEF DESCRIPTION OF THE DRAWINGS

FIG. 4 is a diagram describing an outline of a pattern measurement process flow according to an embodiment of the present invention.

FIG. 8 is a diagram illustrating an example of the configuration of a pattern measurement device according to an embodiment of the present invention.

DESCRIPTION OF THE PREFERRED EMBODIMENTS

An embodiment of a pattern measurement device according to the present invention and a pattern measurement method according to the present invention is described in detail with reference to the accompanying drawings.

Embodiment

First, describing a clear definition of a CD-gap, a difference between a CD value (or a CDCD-SEM) obtained by a CD-SEM and a CD value (or a CDContour) calculated from an SEM contour is referred to as the CD-gap. The CD-gap is defined to be equal to a value of |CDCD-SEM−CDContour|.

Figure 3A:
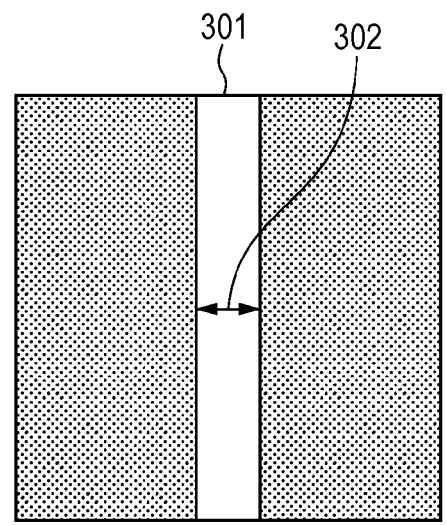
FIG. 3A is a diagram describing a CD-gap (the width of a line).
Figure 3B:
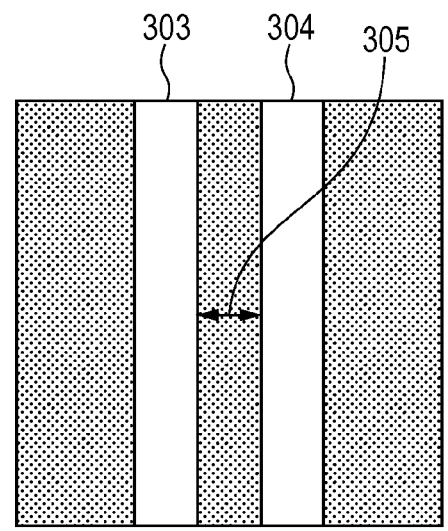
FIG. 3B is a diagram describing a CD-gap (an interval between lines).
Figure 3C:
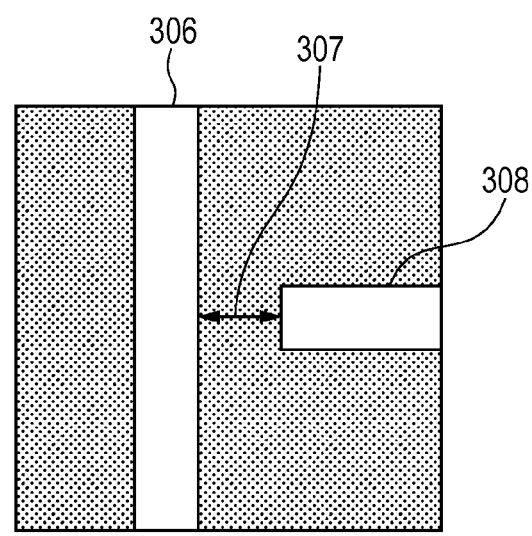
FIG. 3C is a diagram describing a CD-gap (an interval between a line and an edge of a line).

Examples of the CD values are the width 302 (illustrated in FIG. 3A) of a line pattern 301, an interval 305 (illustrated in FIG. 3B) between line patterns 303 and 304, an interval 307 (illustrated in FIG. 3C) between a line pattern 306 and an edge of a line pattern 308. Although FIGS. 3A to 3C illustrate the one-dimensional portions (for example, the straight line portions), the same applies to two-dimensional portions (for example, corners).

Figure 2A:
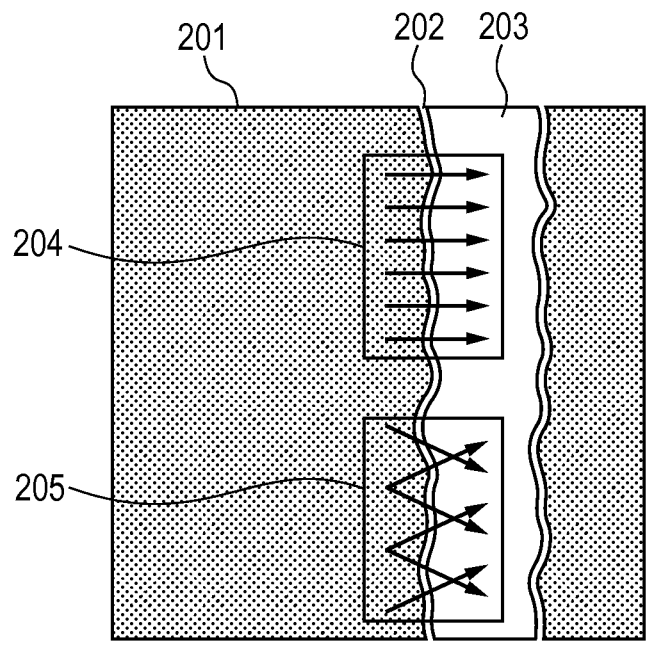
FIG. 2A is a diagram illustrating an outline for positions on the contour of a circuit pattern (an image of the transferred pattern).
Figure 2B:
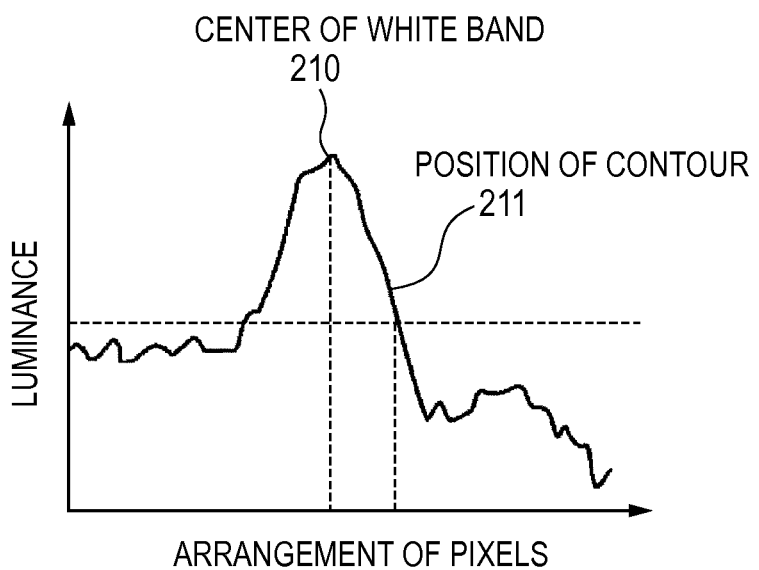
FIG. 2B is a diagram illustrating the outline for the positions on the contour of the circuit pattern (and describes a method for analyzing a luminance profile).

Subsequently, a factor of generating the CD-gap is described with reference to FIG. 2A. The CD-SEM acquires a secondary electron luminance profile in the horizontal coordinate direction (direction indicated by a reference numeral 204 in FIG. 2A) of an image 201, analyzes the luminance profile, and thereby measures dimensions of a circuit pattern. On the other hand, as described in PTL 1, the SEM contour is extracted by acquiring a secondary electron luminance profile in the normal direction (indicated by the reference numeral 204 in FIG. 2A) of the white band (indicated by the reference numeral 202 in FIG. 2A) and analyzing the luminance profile in an existing method of extracting an SEM contour. For example, as illustrated in FIG. 2B, a peak luminance value is defined as the center 210 of the white band. Then, the pixel position, of the pixels located around the center 210 of the white band, whose luminance value is equal to or larger than a predetermined luminance value is defined as a position 211 of the contour. In the OPC model calibration process, however, an image edge of a transferred pattern is distorted, making the scanning direction of the luminance profile tend to be unstable. The known document 4 concludes that the instability in the acquisition direction of the luminance profile reduces the accuracy of extracting an SEM contour, which generates the CD-gap.

In the contour-based calibration, a one-dimensional CD value obtained by a CD-SEM and a two-dimensional SEM contour are used as calibration data, and an inconsistency that occurs due to measurement of the same position or the presence of the CD-gap causes a reduction in the accuracy of the calibration. Thus, it is necessary to use the method of extracting an SEM contour in consideration of suppression of the CD-gap as described in the known document 4.

Next, sampling of an SEM contour is described with reference to FIG. 1C. It is assumed that an SEM contour 106 of a circuit pattern is extracted from an SEM image and is a piecewise continuous curve. The SEM contour 106 is represented by actual two-dimensional positional coordinate values on the image. Sampling of the SEM contour 106 as a group of discrete points as indicated by a reference numeral 107 is referred to as sampling of the SEM contour in the present description. In the sampling, intervals between the discrete points that form the SEM contour may not be equal to each other. In addition, since the SEM contour 106 is used by a calculator, the SEM contour may be held as a group of discrete points with a practical and sufficient resolution (of, for example, approximately 1/100 pixels).

In the embodiment of the present invention, the sampling is carried out after positional coordinate values of a SEM contour of a transferred circuit pattern are calculated. In the embodiment of the present invention, in order to make the two-dimensional positional coordinates of the SEM contour discrete at appropriate intervals, the sampling is carried out on the basis of the SEM contour shape in such a manner as to minimize an allowable error (or a sampling error) specified by a user of the device.

As described above, since the CD-gap occurs due to a reduction in the accuracy of extracting the SEM contour, the sampling needs to be carried out in consideration of the sampling error and a reduction in the CD-gap to improve the accuracy of the OPC model calibration. Next, a pattern measurement process in the embodiment is described. A detailed configuration of a pattern measurement device that executes processes is described later with reference to FIG. 8.

(Main Process)

Main operations of the pattern measurement device according to the present invention are simply described with reference to FIG. 4. First, an arithmetic unit 801 (SEM contour extraction program 821) extracts a SEM contour of a circuit pattern from a SEM image (S401).

The extraction of the SEM contour using the method described in the known document 4 enables it to significantly reduce CD-gap and perform the contour-based calibration with high accuracy.

Figure 7A:
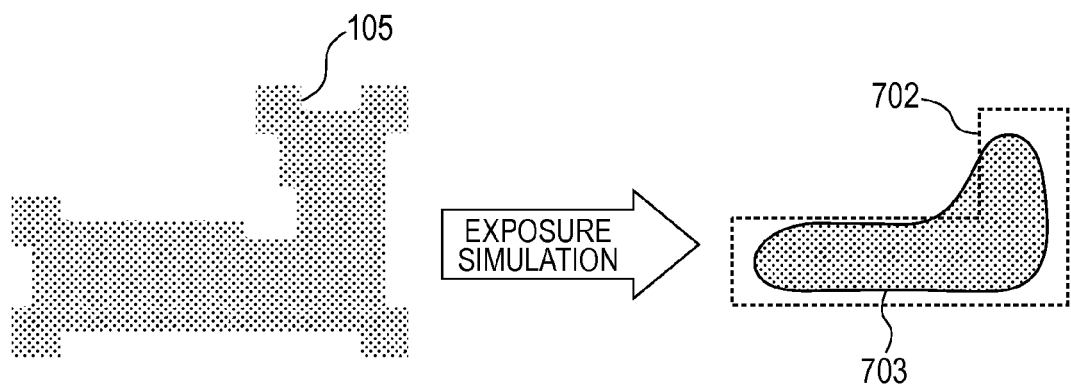
FIG. 7A is a diagram illustrating the case where an estimated SEM contour from the mask edge is simulated with an exposure simulator.

Next, the arithmetic unit 801 (SEM contour extraction program 821) instructs an exposure simulator 841 to calculate the SEM contour, and the exposure simulator 841 calculates to estimate the SEM contour on a water from a mask edge (S402). The estimated SEM contour is referred to as an estimated SEM contour (indicated by a reference numeral 703 in FIG. 7A).

Figure 1A:
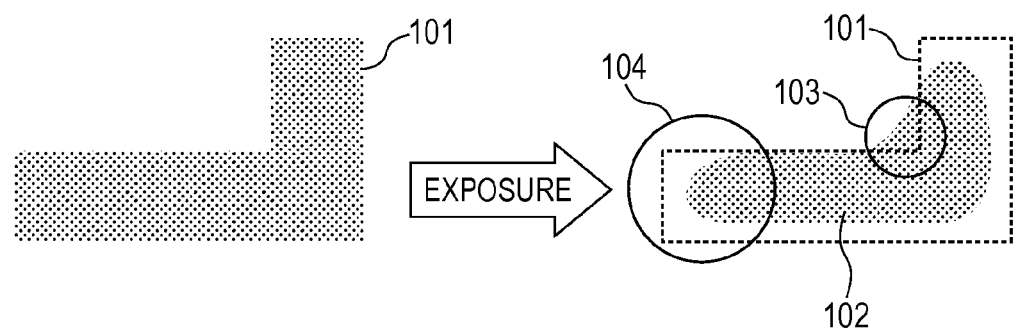
FIG. 1A is a diagram illustrating a relationship between the photomask shape and the transferred circuit pattern shape in a photolithography process (without OPC).
Figure 1B:
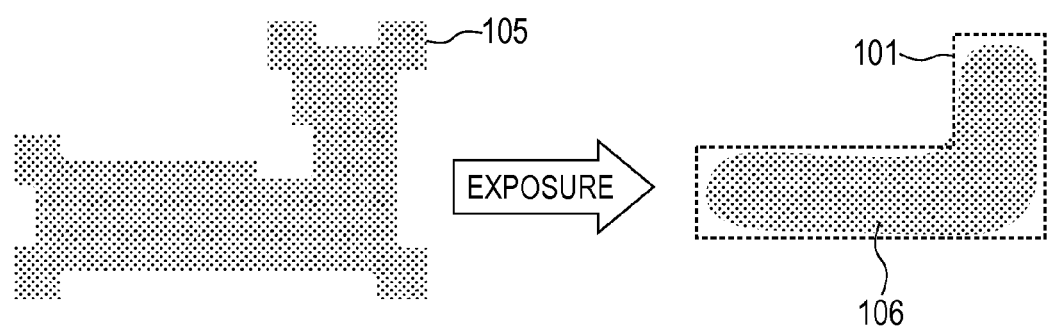
FIG. 1B is a diagram illustrating a relationship between the photomask shape and the transferred circuit pattern shape in the photolithography process (with OPC).
Figure 1C:
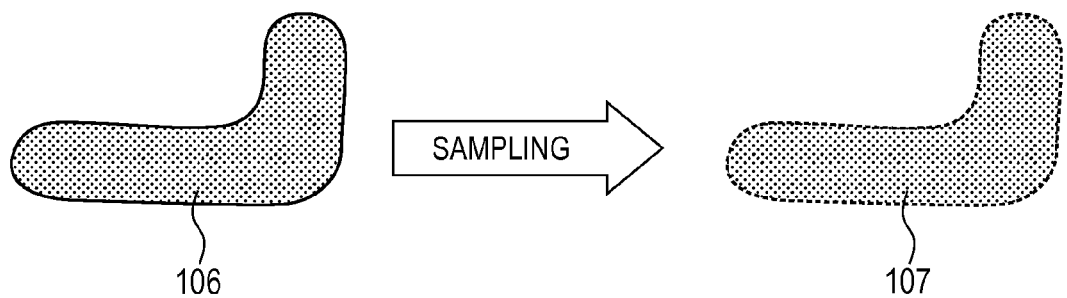
FIG. 1C is a diagram illustrating a relationship between the photomask shape and the transferred circuit pattern shape in the photolithography process (with an SEM contour sampled).
Figure 7B:
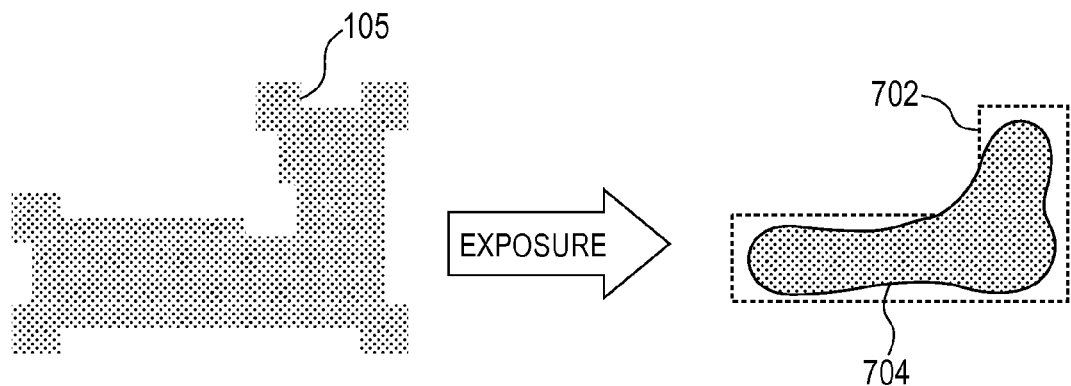
FIG. 7B is a diagram illustrating an SEM contour of a circuit pattern actually exposed through the same mask edge.

Specific examples of the estimated SEM contour obtained by exposure simulation are illustrated in FIG. 7 of the known document 2 and FIG. 1 of a known document 5 (I. Kusnadi, et al., "Contour-based self-aligning calibration of OPC models," Proceedings of SPIE, Vol. 7638, 76382M1-8, 2010).

In a process first executed, the SEM contour that is uniformly sampled may be input to the exposure simulator 841. In this case, the accuracy of estimating the SEM contour is low, and the simulation result is incomplete. A process described later is a process for improving the accuracy of the estimation, and two-dimensional positional coordinates of the SEM contour significantly different from an estimated SEM contour are sequentially added as sampling points.

An estimated SEM contour may be calculated by performing a function approximation on a sampled SEM contour using a curve approximation method with a piecewise approximation function {described in the sixth chapter of a known document 6 (Mikio Takagi, et al., "New Edition Image Analysis Handbook," University of Tokyo Press, 2004)} and may be used instead of an estimated SEM contour output from the exposure simulator.

Figure 5A:
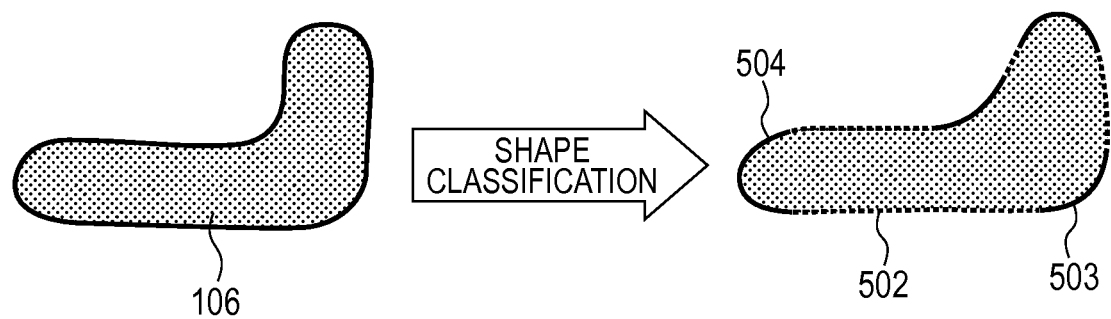
FIG. 5A is a diagram describing shape classification of an SEM contour and sampling for each shape.

Then, the arithmetic unit 801 (shape classification program 822) classifies each of the curves (including straight lines) of the SEM contour and estimated SEM contour into a one-dimensionally shaped portion (a straight line portion indicated by a reference numeral 502 in FIG. 5A) and two-dimensionally shaped portions (a corner indicated by a reference numeral 503 in FIG. 5A and an EOL indicated by a reference numeral 504 in FIG. 5A) (S403). Details of the classification process are described later.

Next, the arithmetic unit 801 (sampling program 823) samples the SEM contour on the basis of the type of the SEM contour shape (S404). Specifically, the arithmetic unit 801 (sampling program 823) executes an "SEM contour sampling process (described later) on the one-dimensionally shaped portion" so as to sample the one-dimensionally shaped portion of the SEM contour. As a result, the straight line portion 502 (illustrated on the left side of FIG. 5B) of the SEM contour is sampled as indicated by a reference numeral 505 on the right side of FIG. 5B.

The arithmetic unit 801 (sampling program 823) executes an "SEM contour sampling process (described later) on the two-dimensionally shaped portions" so as to sample the two-dimensionally shaped portions of the SEM contour. As a result, the corner 503 (illustrated on the left side of FIG. 5C) of the SEM contour is sampled as indicated by a reference numeral 506 on the right side of FIG. 5C. In addition, the EOL 504 of the SEM contour is sampled as indicated by a reference numeral 507 on the right side of FIG. 5D.

Then, the arithmetic unit 801 repeats S402 to S404 until a sampling error permitted by a user is satisfied. If calculation time is limited, the process is not repeated but terminated. Even in this case, the accuracy of the OPC model calibration increases more than sampling of an SEM contour at regular intervals.

As described above, according to the present invention, the process illustrated in FIG. 4 is executed to sample the SEM contour.

(Configuration of Pattern Measurement Device)

The configuration of the pattern measurement device that executes the process according to the embodiment of the present invention is described with reference to FIG. 8.

As illustrated in FIG. 8, the pattern measurement device 800 has the arithmetic unit 801, a main storage device 810, a network adapter 802, an auxiliary storage device 803, an input device 804, and an output device 805. The pattern measurement device 800 is connected through a network 850 to a CD-SEM 840 in such a manner to be able to receive CD data 830 and image data 831 from the CD-SEM 840. In addition, the pattern measurement device 800 is connected through the network 850 to an exposure simulator 841 in such a manner as to be able to receive estimated SEM contour data 834 from the exposure simulator 841. The auxiliary storage device 803 includes a hard disk drive (HDD) and a solid state drive (SSD). The input device 804 includes a trackball, a keyboard, a scanner, and a Blu-ray disc recordable drive (BD-RE D) (Blu-ray is a registered trademark). The output device 805 includes a display, a printer, and a BD-RE D.

The arithmetic unit 801 is a central processing unit (CPU) of a computer and achieves various functions by executing a program loaded in the main storage device 810 composed of a dynamic random access memory (DRAM).

The SEM contour extraction program 821, the shape classification program 822, and the sampling program 823 are stored in the main storage device 810. The data stored in the main storage device 810 is the CD data 830, the image data 831, mask edge data 832, SEM contour data 833, estimated SEM contour data 834, and sampled SEM contour data 835. Programs and data are transmitted/received between the main storage device 810 and the auxiliary storage device 803 in such a manner that consistency of the programs and data is maintained while various programs and data are stored in the main storage device 810 and the auxiliary storage device 803.

The programs stored in the main storage device 810 achieve functions of an SEM contour extracting section, a shape classifying section, and a sampling section. The software programs are composed of modules including the sections. As actual hardware, a controller such as the CPU reads the software programs from the storage device such as the HDD, and executes the software programs, thereby loading the sections into the main storage device. Each of the sections of the SEM contour extracting section, the shape classifying section, and the sampling section are thus generated on the main storage device.

The software programs are in the form of installable files or executable files and can be stored in a computer-readable recording medium such as a CD-ROM, a flexible disk (FD), a CD-R, and a digital versatile disc (DVD) to be provided. The software programs may be downloaded through a network and provided or distributed.

The SEM contour extraction program 821 executes step S401 in FIG. 4. The SEM contour extraction program 821 acquires the CD data 830 and the image data 831 from the CD-SEM 840 through the network 850 in the process of S401 illustrated in FIG. 4 and stores the acquired data in the auxiliary storage device 803. The image data 831 is represented by coordinate positions and luminance values corresponding to the coordinate positions. During the execution of step S401 the image data 831 is copied from the auxiliary storage device 803 to the main storage device 810. Then, the SEM contour extraction program 821 executes a process of extracting an SEM contour, generates the SEM contour data 833, and stores the SEM contour data 833 in the main storage device 810 or the auxiliary storage device 803.

In step S402 in FIG. 4, the exposure simulator 841 is operated in accordance with an instruction from the SEM contour extraction program 821. The exposure simulator 841 reads the mask edge data 832 and the CD data 830 from the auxiliary storage device 803, copies the mask edge data 832 and the CD data 830 into the main storage device 810, and executes a process of simulating the estimated SEM contour data 834 on the basis of the mask edge data 832.

If the main storage device 810 or the auxiliary storage device 803 has stored therein the sampled SEM contour data 835, the sampled SEM contour data 835 can be used to improve the accuracy of the exposure simulation.

Lastly, the SEM contour extraction program 821 stores the estimated SEM contour data 834 in the main storage device 810 or the auxiliary storage device 803.

The sampling program 823 executes step S404 in FIG. 4. The sampling program 823 uses the SEM contour data 831 and the estimated SEM contour 834 to execute the sampling process, generates the sampled SEM contour data 835, and stores the sampled SEM contour data 835 in the main storage device 810 and the auxiliary storage device 803. The process executed by the sampling program 823 is described in detail later with reference to FIGS. 9A and 9B.

(Classification of Contour)

Figure 5B:
FIG. 5B is a diagram describing shape classification of the SEM contour and an estimated SEM contour (sampling of a straight line portion).
Figure 5C:
FIG. 5C is a diagram describing the shape classification of the SEM contour and the estimated SEM contour (sampling of a corner portion).
Figure 5D:
FIG. 5D is a diagram describing the shape classification of the SEM contour and the estimated SEM contour (sampling of an EOL).

First, the process of classifying each of curves (including straight lines) forming an SEM contour and estimated SEM contour into a one-dimensionally shaped portion (the straight line portion indicated by the reference numeral 502 in FIG. 5B) and two-dimensionally shaped portions (the corner indicated by the reference numeral 503 in FIG. 5C and the EOL indicated by the reference numeral 505 in FIG. 5D) is described in detail.

Figure 6A:
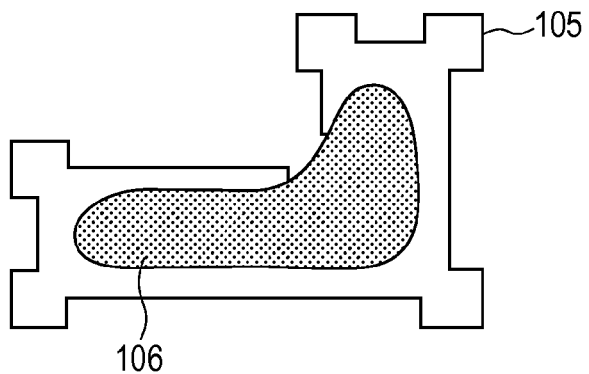
FIG. 6A is a diagram describing the shape classification of the SEM contour in detail {or a diagram illustrating a relationship between a mask edge and the SEM contour (or the estimated SEM contour)}.
Figure 6B:
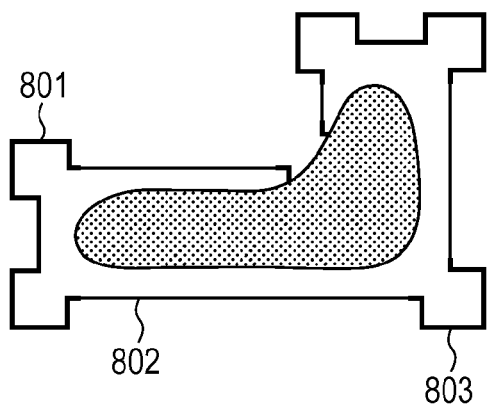
FIG. 6B is a diagram describing the shape classification of the SEM contour in detail (or a diagram describing classification of the mask edge shape).

First, the shape classification program 822 classifies a mask edge (indicated by a reference numeral 105 in FIG. 6A) into a one-dimensionally shaped portion (a straight line portion indicated by a reference numeral 802 in FIG. 6B) and two-dimensionally shaped portions (a corner indicated by a reference numeral 801 in FIG. 6B and an EOL indicated by a reference numeral 803 illustrated in FIG. 6B). In this case, the method described in the known document 4 may be used, or the user of the device may specify small sections in advance.

Figure 6C:
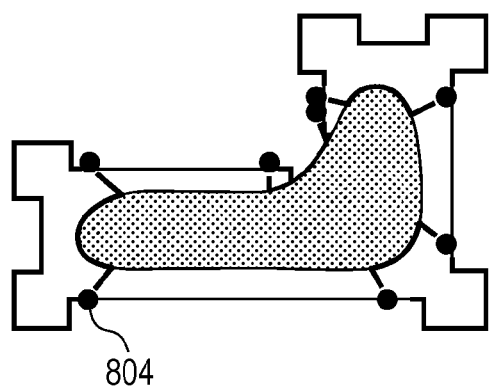
FIG. 6C is a diagram describing the shape classification of the SEM contour in detail {or a diagram describing mapping of classification of the mask edge to the SEM contour (or the estimated SEM contour)}.
Figure 6D:
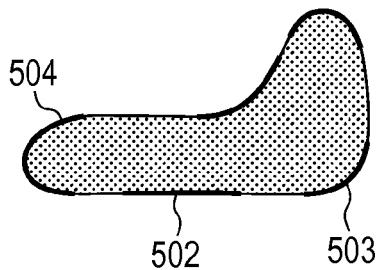
FIG. 6D is a diagram describing the shape classification of the SEM contour in detail (or a diagram illustrating the classified SEM contour (or the estimated SEM contour).

Lastly, as illustrated in FIG. 6C, corresponding relationships between the mask edge and the SEM contour are calculated (this process is hereinafter referred to as mapping process). The mapping process is a process of calculating the corresponding relationships between a section including a curve forming the mask edge and a section corresponding to the section of the mask edge and included in the SEM contour.

In this case, the method described in the known document 4 may be used, or an iterative closest point (ICP) method or the method disclosed in JP-A-2006-351888 may be used to calculate the corresponding relationships and specify sections of the one-dimensionally shaped portion and two-dimensionally shaped portions.

In the mapping process, sections of the one-dimensionally shaped portion and two-dimensionally shaped portions of the estimated SEM contour (indicated by a reference numeral 703 in FIG. 7A) are specified in the same procedure.

Note that all sections of the SEM contour may be treated as a single basic shape. For example, a contact hole or a via hole within a circuit pattern has a circle or ellipse shape, and hence, all sections are sampled as a corner.

The user of the device may specify sections of the one-dimensionally shaped portion (straight line portion indicated by the reference numeral 502 in FIG. 5B) and two-dimensionally shaped portions (the corner indicated by the reference numeral 503 in FIG. 5C and the EOL indicated by the reference numeral 504 in FIG. 5D) for the SEM contour and the estimated SEM contour. In this case, the process of classifying a contour can be omitted.

(SEM Contour Sampling Process)

Figure 9A:
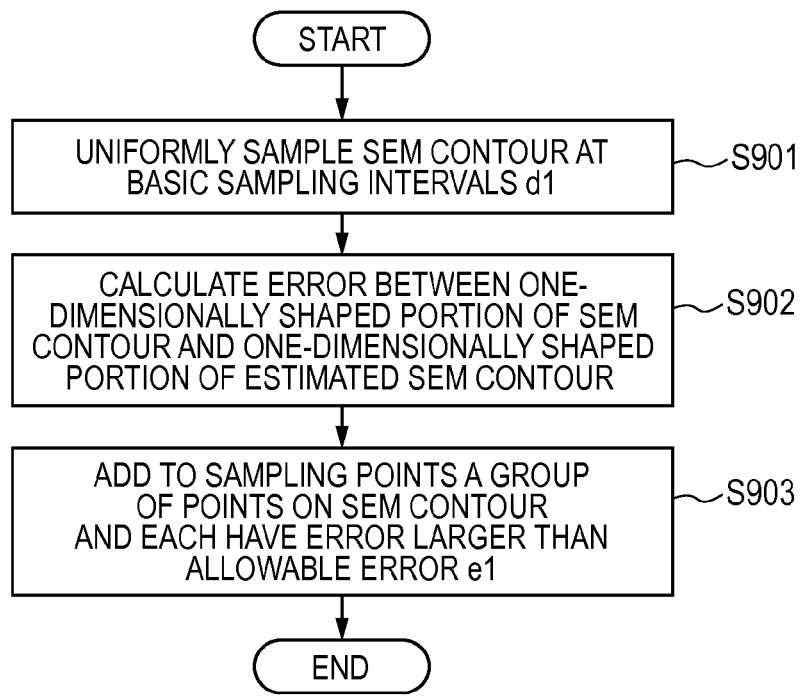
FIG. 9A is a diagram describing an outline of a process flow of sampling an SEM contour in S404 illustrated in FIG. 4.
Figure 9B:
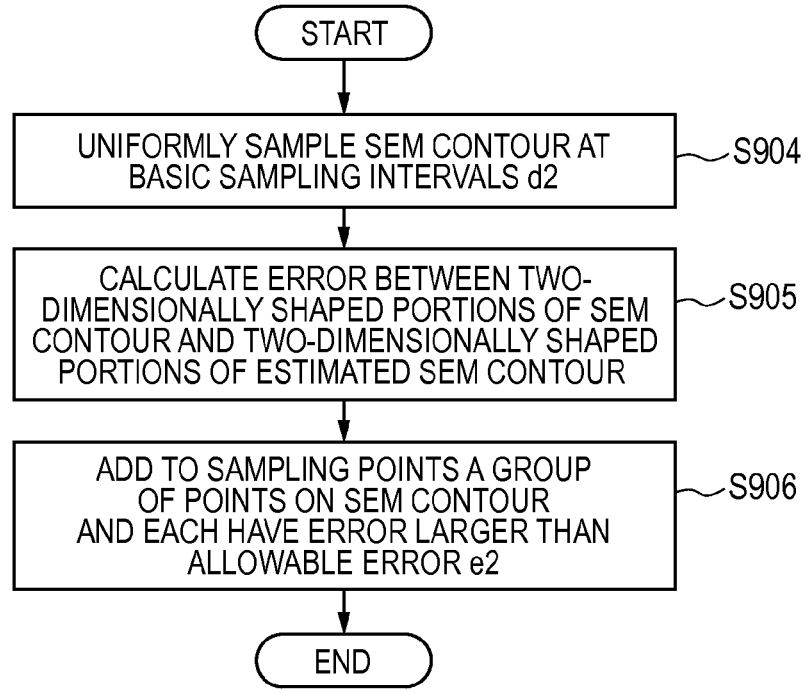
FIG. 9B is a diagram describing the outline of a process flow of sampling an SEM contour in S404 illustrated in FIG. 4.

Next, the SEM contour sampling is described in detail with reference to FIGS. 9A and 9B. First, a process of sampling the one-dimensionally shaped portion (indicated by the reference numeral 502 in FIG. 5B) is described.

(SEM Contour Sampling Process on One-Dimensional Portion)

In S901, the sampling program 823 uniformly samples the SEM contour at basic sampling intervals d1 nm. This process can be skipped, though; sampling is carried out within a range of a predetermined allowable error in that case.

In S902, the sampling program 823 calculates an error between the one-dimensionally shaped portion of the SEM contour and the one-dimensionally shaped portion of the estimated SEM contour. The error between the one-dimensionally shaped portions is represented by an Euclidean distance between the SEM contour (indicated by a reference numeral 704 in FIG. 7B) on the wafer and the estimated SEM contour (indicated by a reference numeral 703 in FIG. 7A). In such a case, a method of calculating the distance uses any of the following six methods {(i) to (vi)}.

Figure 10A:
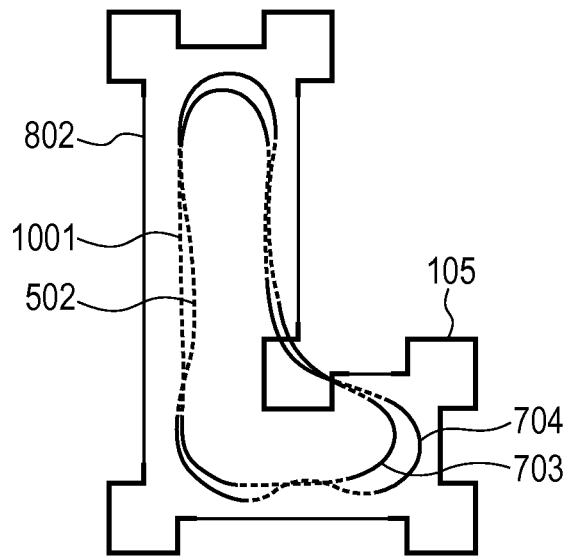
FIG. 10A is a diagram describing a process of sampling a one-dimensionally shaped portion of an SEM contour.
Figure 10B:
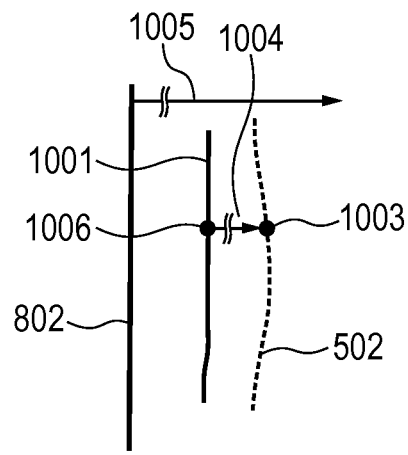
FIG. 10B is a diagram describing a method for calculating a sampling error of the one-dimensionally shaped portion.

Explaining the method of the type (i) with reference to FIGS. 10A and 10B, the sampling program 823 uses an arbitrary single point (indicated by a reference numeral 1006 in FIG. 10B) on an estimated SEM contour 1001 as a standard point. After the sampling program 823 calculates a single point (indicated by a reference numeral 1003 in FIG. 10B) at which a line (indicated by a reference numeral 1004 in FIG. 10B) which starts from the standard point and is in parallel to a normal (indicated by a reference numeral 1005 in FIG. 10B) of a mask edge 802 crosses the SEM contour 502, it calculates an Euclidean distance between the two points.

Figure 10C:
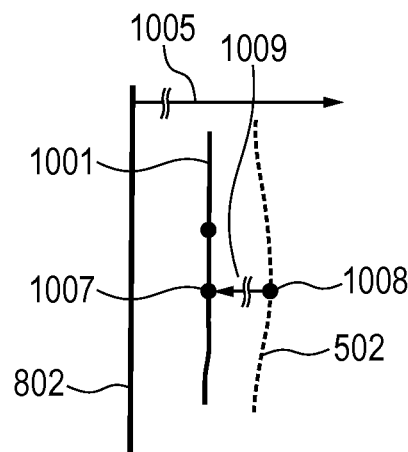
FIG. 10C is a diagram describing a method for calculating a sampling error of the one-dimensionally shaped portion.

Explaining the method of the type (ii) with reference to FIGS. 10A and 10C, the sampling program 823 uses an arbitrary single point (indicated by a reference numeral 1008 in FIG. 10C) on the SEM contour 502 as a standard point. After the sampling program 823 calculates a single point (indicated by a reference numeral 1007 in FIG. 10C) at which a line (indicated by a reference numeral 1009 in FIG. 10C) which starts from the standard point and is in parallel to the normal (indicated by the reference numeral 1005 in FIG. 10B) of the mask edge 802 crosses the estimated SEM contour 1001, it calculates an Euclidean distance between the two points.

Figure 10D:
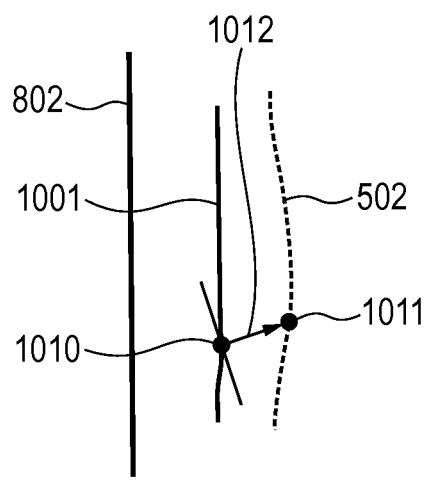
FIG. 10D is a diagram describing a method for calculating a sampling error of the one-dimensionally shaped portion.

Explaining the method of the type (iii) with reference to FIGS. 10A and 10D, the sampling program 823 uses an arbitrary single point (indicated by a reference numeral 1010 in FIG. 10D) on the estimated SEM contour 1001 as a standard point. After the sampling program 823 calculates a single point (indicated by a reference numeral 1011 in FIG. 10D) at which a normal (indicated by a reference numeral 1012 in FIG. 10D) of the estimated SEM contour 1001 at the standard point crosses the SEM contour 502, it calculates an Euclidean distance between the two points.

Figure 10E:
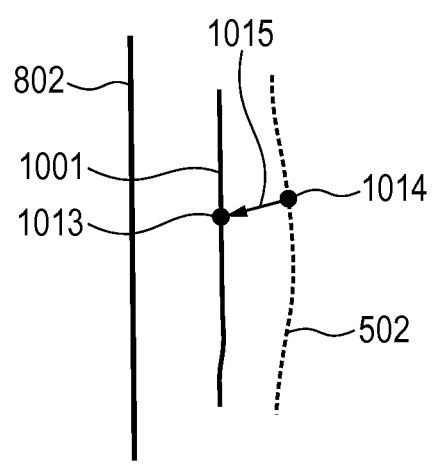
FIG. 10E is a diagram describing a method for calculating a sampling error of the one-dimensionally shaped portion.

Explaining the method of the type (iv) with reference to FIGS. 10A and 10E, the sampling program 823 uses an arbitrary single point (indicated by a reference numeral 1014 in FIG. 10E) on the SEM contour 502 as a standard point. After the sampling program 823 calculates a single point (indicated by a reference numeral 1013 in FIG. 10E) at which a normal (indicated by a reference numeral 1015 in FIG. 10E) of the SEM contour 502 at the standard point crosses the estimated SEM contour 1001, it calculates an Euclidean distance between the two points.

Figure 10F:
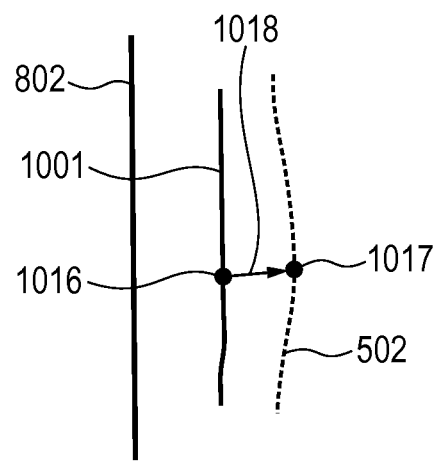
FIG. 10F is a diagram describing a method for calculating a sampling error of the one-dimensionally shaped portion.

Explaining the method of the type (v) with reference to FIGS. 10A and 10F, the sampling program 823 uses an arbitrary single point (indicated by a reference numeral 1016 in FIG. 10F) on the estimated SEM contour 1001 as a standard point. After the sampling program 823 calculates a single point (indicated by a reference numeral 1017 in FIG. 10F) on the SEM contour 502 with the shortest Euclidean distance to the SEM contour 502, it calculates an Euclidean distance between the two points.

Figure 10G:
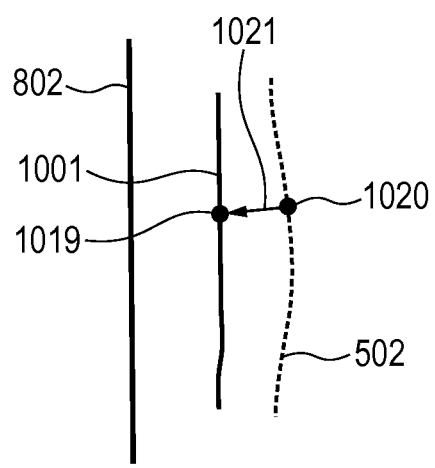
FIG. 10G is a diagram describing a method for calculating a sampling error of the one-dimensionally shaped portion.

Explaining the method of the type (vi) with reference to FIGS. 10A and 10G, the sampling program 823 uses an arbitrary single point (indicated by a reference numeral 1020 in FIG. 10G) on the SEM contour 502 as a standard point. After the sampling program 823 calculates a single point (indicated by a reference numeral 1019 in FIG. 10G) on the estimated SEM contour 502 with the shortest Euclidean distance to the estimated SEM contour 1001, it calculates an Euclidean distance between the two points.

The distance calculation method of the type (i) has the largest degree of the reduction in the CD-gap. Especially, when the SEM contour is calculated using the method described in the known document 4, the normal direction of the mask edge corresponds to the acquisition direction of the secondary electron profile, whereby a sampling result suppressing the CD-gap to a low value can be obtained.

As illustrated in FIG. 1 of the known document 5, it is necessary to note that a calculated error may vary depending on whether a point on an estimated SEM contour or a point on an SEM contour is used as a standard point.

Make sure to calculate an error between the SEM contour and the estimated SEM contour in all regions of the SEM contour although this is obvious.

In order to calculate the error between the SEM contour and the estimated SEM contour in all the regions of the SEM contour, an interval between standard points to be selected from a contour serving as a standard is sufficiently shorter than the standard sampling intervals d1 nm (for example, approximately d1/100 nm).

Lastly, in S903, the sampling program 823 adds to sampling points a point with an error larger than an allowable error e1 of the one-dimensionally shaped portion among the points forming the SEM contour obtained in the aforementioned step S902.

In the methods (i), (iii), and (v), since the standard points are on the estimated SEM contour 1001, the calculated points (indicated by the reference numeral 1003 illustrated in FIG. 10B, the reference numeral 1011 illustrated in FIG. 10D, and the reference numeral 1017 illustrated in FIG. 10F) on the SEM contour 502 are sampling points.

In the methods (ii), (iv), and (vi), the standard points on the SEM contour 502 (indicated by the reference numeral 1008 illustrated in FIG. 10C, the reference numeral 1014 illustrated in FIG. 10E, and the reference numeral 1020 illustrated in FIG. 10G) are sampling points.

In each of the methods, positional coordinates of the sampling points on the SEM contour have resolutions of actual numbers.

(SEM Contour Sampling Process on Two-Dimensionally Shaped Portion)

Next, a process of sampling a two-dimensionally shaped portion is described. In S904, the SEM contour is uniformly sampled at basic sampling intervals d2 nm. This step can be skipped, though; sampling is carried out within a range of an allowable error in the same manner as the SEM contour sampling process on a one-dimensionally shaped portion.

In S905, the sampling program 823 calculates an error between the two-dimensionally shaped portions of the SEM contour and the two-dimensionally shaped portions of the estimated SEM contour. The error between the two-dimensionally shaped portions is represented by an Euclidean distance between the SEM contour (indicated by the reference numeral 704 in FIG. 7A) and the estimated SEM contour (indicated by the reference numeral 703 in FIG. 7A). As a result, a method of calculating the distance uses any of the following six methods {(i) to (vi)}, like the SEM contour sampling process on a one-dimensionally shaped portion. In addition, the EOL is described below as an example with reference to FIGS. 11A to 11G, the same applies to the corner.

Figure 11A:
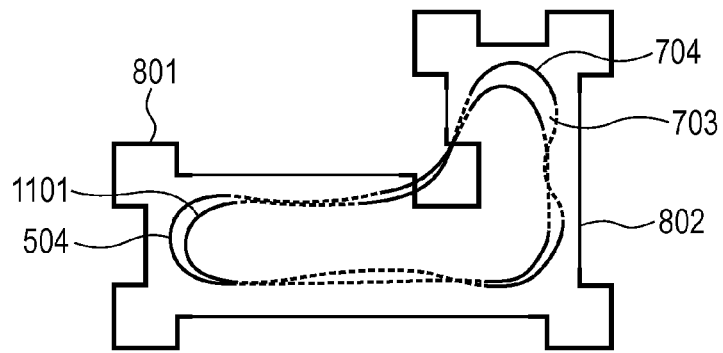
FIG. 11A is a diagram describing a process of sampling a two-dimensionally shaped portion of an SEM contour.
Figure 11B:
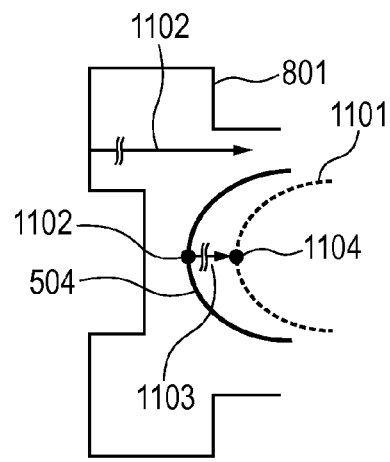
FIG. 11B is a diagram describing a method for calculating a sampling error of the two-dimensionally shaped portion.

Explaining the method of the type (i) with reference to FIGS. 11A and 11B, the sampling program 823 uses an arbitrary single point (indicated by a reference numeral 1102 in FIG. 11B) on an estimated SEM contour 504 as a standard point. After the sampling program 823 calculates a single point (indicated by a reference numeral 1104 in FIG. 11B) at which a line (indicated by a reference numeral 1103 in FIG. 11B) which starts from the standard point and is in parallel to a normal (indicated by a reference numeral 1102 in FIG. 11B) of a mask edge 801 crosses an SEM contour 1101, it calculates an Euclidean distance between the two points.

Figure 11C:
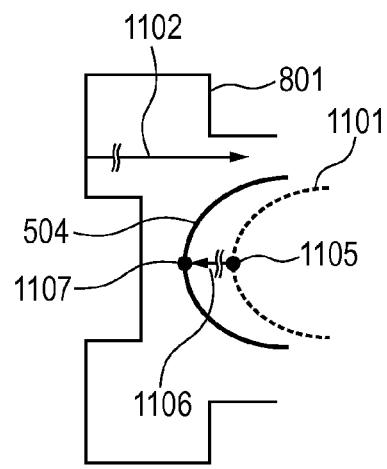
FIG. 11C is a diagram describing a method for calculating a sampling error of the two-dimensionally shaped portion.

Explaining the method of the type (ii) with reference to FIGS. 11A and 11C, the sampling program 823 uses an arbitrary single point (indicated by a reference numeral 1105 in FIG. 11C) on the SEM contour 1101 as a standard point. After the sampling program 823 calculates a single point (indicated by a reference numeral 1107 in FIG. 11C) at which a line (indicated by a reference numeral 1106 in FIG. 11C) which starts from the standard point and is in parallel to the normal direction (indicated by a reference numeral 1102 in FIG. 11C) of the mask edge 801 crosses the estimated SEM contour 504, it calculates an Euclidean distance between the two points.

Figure 11D:
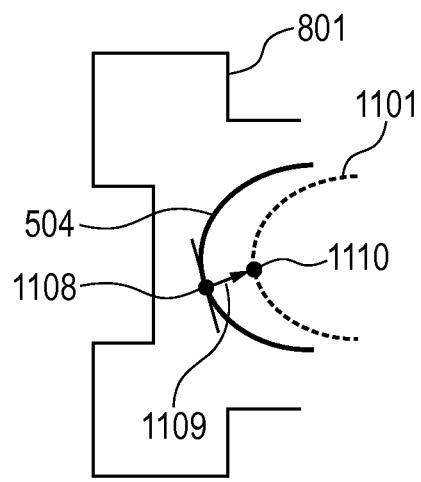
FIG. 11D is a diagram describing a method for calculating a sampling error of the two-dimensionally shaped portion.

Explaining the method of the type (iii) with reference to FIGS. 11A and 11D, the sampling program 823 uses an arbitrary single point (indicated by a reference numeral 1108 in FIG. 11D) on the estimated SEM contour 504 as a standard point. After the sampling program 823 calculates a single point (indicated by a reference numeral 1110 in FIG. 11D) at which a normal (indicated by a reference numeral 1109 in FIG. 11D) of the estimated SEM contour at the standard point crosses the SEM contour 1101, it calculates an Euclidean distance between the two points.

Figure 11E:
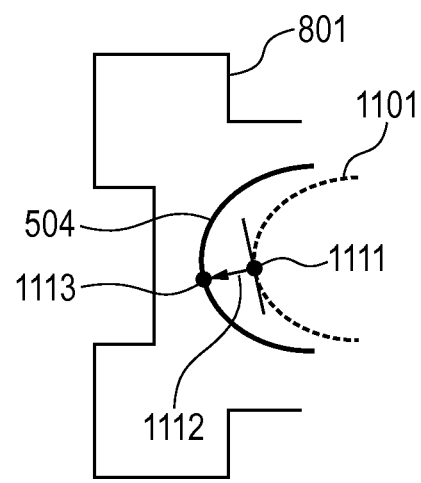
FIG. 11E is a diagram describing a method for calculating a sampling error of the two-dimensionally shaped portion.

Explaining the method of the type (iv) with reference to FIGS. 11A and 11E, the sampling program 823 uses an arbitrary single point (indicated by a reference numeral 1111 in FIG. 11E) on the SEM contour 1101 as a standard point. After the sampling program 823 calculates a single point (indicated by a reference numeral 1113 in FIG. 11E) at which a normal (indicated by a reference numeral 1112 in FIG. 11E) of the SEM contour 1101 at the standard point crosses the estimated SEM contour 504, it calculates an Euclidean distance between the two points.

Figure 11F:
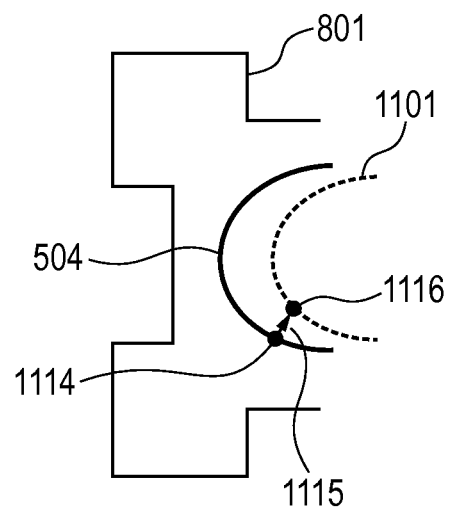
FIG. 11F is a diagram describing a method for calculating a sampling error of the two-dimensionally shaped portion.

Explaining the method of the type (v) with reference to FIGS. 11A and 11F, the sampling program 823 uses an arbitrary single point (indicated by a reference numeral 1114 in FIG. 11F) on the estimated SEM contour 504 as a standard point. After the sampling program 823 calculates a single point (indicated by a reference numeral 1116 in FIG. 11F) on the SEM contour 1101 with the shortest Euclidean distance to the SEM contour 1101, it calculates an Euclidean distance between the two points.

Figure 11G:
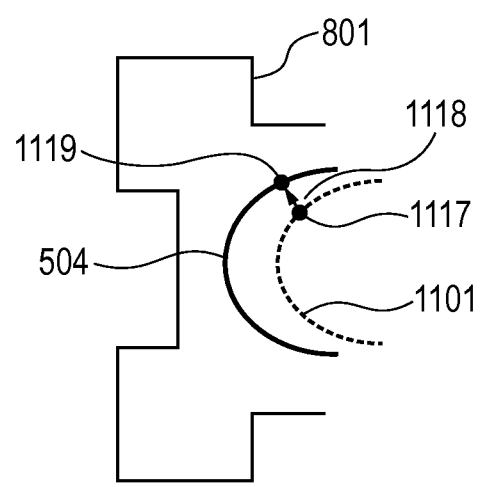
FIG. 11G is a diagram describing a method for calculating a sampling error of the two-dimensionally shaped portion.

Explaining the method of the type (vi) with reference to FIGS. 11A and 11G, the sampling program 823 uses an arbitrary single point (indicated by a reference numeral 1117 in FIG. 11G) on the SEM contour 1101 as a standard point. After the sampling program 823 calculates a single point (indicated by a reference numeral 1119 in FIG. 11G) on the estimated SEM contour 504 with the shortest Euclidean distance to the estimated SEM contour 504, it calculates an Euclidean distance between the two points.

If the two-dimensionally shaped portion is the EOL, the distance calculation method of the type (i) has the largest degree of the reduction in the CD-gap, like the case of the one-dimensionally shaped portion. Especially, when the SEM contour is calculated using the method described in the known document 4, the normal direction of the mask edge corresponds to the acquisition direction of the secondary electron profile, whereby a sampling result that suppresses the CD-gap to a low value can be obtained.

Lastly, in S906, the sampling program 823 adds to sampling points a point with an error larger than an allowable error e2 of the two-dimensionally shaped portion among the points forming the SEM contour obtained in the step S905. Different basic sampling intervals and an allowable error may be defined for the corner and the EOL each.

As illustrated in FIG. 1 of the known document 5, it is necessary to note that a calculated error may vary depending on whether a point on an estimated SEM contour or a point on an SEM contour is used as a standard point.

Make sure to calculate an error between the SEM contour and the estimated SEM contour in all regions of the SEM contour although this is obvious.

In order to calculate the error between the SEM contour and the estimated SEM contour in all the regions of the SEM contour, an interval between standard points to be selected from a contour serving as a standard is sufficiently shorter than the standard sampling intervals d2 nm (for example, approximately d2/100 nm)

In the methods (i), (iii), and (v), since the standard points are on the estimated SEM contour, the calculated points (indicated by the reference numeral 1104 illustrated in FIG. 11B, the reference numeral 1110 illustrated in FIG. 11D, and the reference numeral 1116 illustrated in FIG. 11F) on the SEM contour are sampling points.

In the methods (ii), (iv), and (vi), since the standard points are on the SEM contour, the standard points (indicated by the reference numeral 1105 illustrated in FIG. 11C, the reference numeral 1111 illustrated in FIG. 11E, and the reference numeral 1117 illustrated in FIG. 11G) are sampling points.

In each of the methods, positional coordinates of the sampling points on the SEM contour have resolutions of actual numbers.

The main storage device 810 stores the mask edge data of the circuit pattern of a semiconductor and the image data obtained by imaging the circuit pattern. The SEM contour extracting section (SEM contour extraction program 821) receives the image data, extracts a scanning electron microscope (SEM) contour of the circuit pattern, and causes the exposure simulator 841 to generate data (estimated SEM contour data) of an estimated SEM contour on the basis of the mask edge data and data (SEM contour data) of the extracted SEM contour. The shape classifying section (shape classification program 822) receives the mask edge data, the SEM contour data, and the estimated contour data and classifies the SEM contour data and the estimated SEM contour data into a one-dimensionally shaped contour and a two-dimensionally shaped contour. The SEM contour sampling section (SEM contour sampling program 823) receives the SEM contour data and the estimated SEM contour data and then samples the SEM contour data on the basis of the type of the one-dimensional shape and the type of the two-dimensional shape. Thus, the accuracy of the OPC model calibration can be improved while calculation time required for the OPC model calibration is reduced.

REFERENCE SIGNS LIST

- 800 . . . Pattern measurement device
- 801 . . . Arithmetic unit
- 802 . . . Network adapter
- 803 . . . Auxiliary storage device
- 804 . . . Input device
- 805 . . . Output device
- 810 . . . Main storage device
- 821 . . . SEM contour extraction program
- 822 . . . Shape classification program
- 823 . . . Sampling program
- 830 . . . CD data
- 831 . . . Image data
- 832 . . . Mask edge data
- 833 . . . SEM contour data
- 834 . . . Estimated SEM contour data
- 835 . . . Sampled SEM contour data
- 840 . . . CD-SEM
- 841 . . . Exposure simulator
- 850 . . . Network

The invention claimed is:

1. A pattern measurement device comprising:
a storage section configured to store mask edge data of a circuit pattern of a semiconductor and image data obtained by imaging the circuit pattern;
an SEM contour extracting section configured to receive the image data, extract a scanning electron microscope contour of the circuit pattern, and cause an exposure simulator to generate data of an estimated SEM contour on the basis of the mask edge data and data of the extracted SEM contour;
a shape classifying section configured to receive the mask edge data, the SEM contour data, and the estimated SEM contour data to classify the SEM contour data and the estimated SEM contour data into a one-dimensionally shaped contour and a two-dimensionally shaped contour; and
an SEM contour sampling section configured to receive the SEM contour data and the estimated SEM contour data to sample the SEM contour data on the basis of types of the one-dimensionally and two-dimensionally shaped contours.

2. The pattern measurement device according to claim 1, wherein the SEM contour extracting section extracts from the circuit pattern a contour having a suppressed critical dimension gap that is a difference between the SEM contour and a contour obtained from a value measured by an SEM.

3. The pattern measurement device according to claim 1, wherein the SEM contour sampling section samples the SEM contour data by using an appointed point located on the estimated SEM contour as a standard point, calculating a point at which a line which starts from the appointed point and is in parallel to a normal of the mask edge data crosses the SEM contour, and calculating an Euclidean distance between the two points.

4. The pattern measurement device according to claim 1, wherein the SEM contour sampling section samples the SEM contour data by using an appointed point located on the SEM contour as a standard point, calculating a point at which a line which starts from the appointed point and is in parallel to a normal direction of the mask edge data crosses the estimated SEM contour, and calculating an Euclidean distance between the two points.

5. The pattern measurement device according to claim 1, wherein the SEM contour sampling section samples the SEM contour data by using an appointed point located on the estimated SEM contour as a standard point, calculating a point at which a normal of the estimated SEM contour at the appointed point crosses the SEM contour, and calculating an Euclidean distance between the two points.

6. The pattern measurement device according to claim 1, wherein the SEM contour sampling section samples the SEM contour data by using an appointed point located on the SEM contour as a standard point, calculating a point at which a normal of the SEM contour at the appointed point crosses the estimated SEM contour, and calculating an Euclidean distance between the two points.

7. The pattern measurement device according to claim 1, wherein the SEM contour sampling section samples the SEM contour data by using an appointed point located on the estimated SEM contour as a standard point, calculating a point on the SEM contour with the shortest Euclidean distance between the appointed point and the SEM contour, and calculating an Euclidean distance between the two points.

8. The pattern measurement device according to claim 1, wherein the SEM contour sampling section samples the SEM contour data by using an appointed point located on the SEM contour as a standard point, calculating a point on the estimated SEM contour with the shortest Euclidean distance between the appointed point and the estimated SEM contour, and calculating an Euclidean distance between the two points.

9. The pattern measurement device according to claim 1, wherein the one-dimensionally shaped contour includes at least a straight line portion, and the two-dimensionally shaped contour includes at least a corner and an end of a line.

10. A pattern measurement method comprising steps of:
receiving image data obtained by imaging a circuit pattern of a semiconductor and extracting an SEM contour of the circuit pattern;
causing an exposure simulator to generate data of an estimated SEM contour on the basis of mask edge data of the circuit pattern of the semiconductor and data of the extracted SEM contour;
receiving the mask edge data, the SEM contour data, and the estimated contour data to classify the SEM contour data and the estimated SEM contour data into a one-dimensionally shaped contour and a two-dimensionally shaped contour; and
receiving the SEM contour data and the estimated SEM contour data to sample the SEM contour data on the basis of types of the one-dimensionally and two-dimensionally shaped contours.

11. The pattern measurement method according to claim 10, wherein a contour with a suppressed CD gap which is a difference between the SEM contour and a contour obtained from a value measured by an SEM is extracted from the circuit pattern in the extraction step.

* * * * *